United States Patent
Sakharkar et al.

(10) Patent No.: US 11,331,330 B2
(45) Date of Patent: May 17, 2022

(54) PHYTOCHEMICAL-ANTIBIOTIC COMBINATION FOR THE TREATMENT OF A BACTERIAL INFECTION

(71) Applicant: University of Saskatchewan, Saskatoon (CA)

(72) Inventors: Meena Kishor Sakharkar, Saskatoon (CA); Jian Yang, Saskatoon (CA)

(73) Assignee: University of Saskatchewan, Saskatoon (CA)

(*) Notice: Subject to any disclaimer, the term of this patent is extended or adjusted under 35 U.S.C. 154(b) by 57 days.

(21) Appl. No.: 17/046,164

(22) PCT Filed: May 31, 2019

(86) PCT No.: PCT/CA2019/050752
§ 371 (c)(1),
(2) Date: Oct. 8, 2020

(87) PCT Pub. No.: WO2019/227226
PCT Pub. Date: Dec. 5, 2019

(65) Prior Publication Data
US 2021/0060049 A1    Mar. 4, 2021

Related U.S. Application Data

(60) Provisional application No. 62/679,215, filed on Jun. 1, 2018.

(51) Int. Cl.
*A61K 31/7048* (2006.01)
*A61P 31/04* (2006.01)
*A61K 31/192* (2006.01)

(52) U.S. Cl.
CPC ........ *A61K 31/7048* (2013.01); *A61K 31/192* (2013.01); *A61P 31/04* (2018.01)

(58) Field of Classification Search
None
See application file for complete search history.

(56) References Cited

FOREIGN PATENT DOCUMENTS

WO    2011060295 A1    5/2011

OTHER PUBLICATIONS

Written Opinion and International Search Report of corresponding International Application No. PCT/CA2019/050752 dated Sep. 4, 2019, 11 pages.
Alexander et al., "Susceptibility to tulathromycin in Mannheimia haemolytica isolated from feedlot cattle over a 3-year period", Frontiers in Microbiology, Oct. 2013, vol. 4, Article 297, pp. 1-8.
Zhou et al., "Pharmacokinetic/Pharmacodynamic Modeling of Tulathromycin against Pasteurella multocida in a Porcine Tissue Cage Model", Frontiers in Pharmacology, Jun. 28, 2017, vol. 8, Article 392, pp. 1-11.
Borges et al., "Antibacterial activity and mode of action of ferulic and gallic acids against pathogenic bacteria", Microbial Drug Resistance, 2013, vol. 19, No. 4, pp. 256-265.
Saavedra et al., "Antimicrobial activity of phenolics and glucosinolate hydrolysis products and their synergy with streptomycin against pathogenic bacteria", Medicinal Chemistry, May 2010, vol. 6 No. 3, pp. 174-183.
Jayaraman et al., "Activity and interactions of antibiotic and phytochemical combinations against Pseudomonas aeruginosa in vitro", International Journal of Biological Sciences, Sep. 2010, vol. 6, No. 6, pp. 556-568.
Rajamanickam et al., "Gallic Acid Potentiates the Antimicrobial Activity of Tulathromycin Against Two Key Bovine Respiratory Disease (BRD) Causing-Pathogens", Frontiers in Pharmacology, Jan. 4, 2019, vol. 9, Article 1486, pp. 1-9.
Nayeem et al., "Gallic Acid: A Promising Lead Molecule for Drug Development", J. App Pharm, 2016, vol. 8. No. 2, pp. 1-4.

*Primary Examiner* — Dale R Miller
(74) *Attorney, Agent, or Firm* — Bereskin & Parr LLP/S.E.N.C.R.L, s.r.l.; Sandra Marone

(57) ABSTRACT

The present application relates to combination treatments for bacterial infections. For example, the application relates to the use of tulathromycin and gallic acid for the treatment of a *Mannheimia haemolytica* and/or *Pasteurella multocida* bacterial infection or a disease, disorder or condition arising from a *Mannheimia haemolytica* and/or *Pasteurella multocida* bacterial infection.

20 Claims, 6 Drawing Sheets

Fig. 4A

**Wild type *Mannheimia haemolytica* ATCC 29702
Combination of GA and Tul**

Fig. 4B

**Combination of GA and Tul against
Wild type *Pasteurella multocida* ATCC 43137**

Fig. 5A

**1G, 2G, 3G of 1/2 MIC of Tul *Mannheimia haemolytica* ATCC 29702 against Tulathromycin**

Fig. 5B

**1G, 2G, 3G of 1/2 MIC of Tul *Mannheimia haemolytica* ATCC 29702 against Gallic Acid**

Fig. 6A

**1G, 2G, 3G of 1/2 MIC of Tul *Pasteurella multocida* ATCC 43137 against Tulathromycin**

Fig. 6B

**1G, 2G, 3G of 1/2 MIC of Tul *Pasteurella multocida* ATCC 43137 against Gallic Acid**

PHYTOCHEMICAL-ANTIBIOTIC COMBINATION FOR THE TREATMENT OF A BACTERIAL INFECTION

CROSS-REFERENCE TO RELATED APPLICATION

This application is a National Stage of co-pending International Application No. PCT/CA2019/050752 filed on May 31, 2019 which claims the benefit of priority from U.S. Provisional Patent Application Ser. No. 62/679,215, filed on Jun. 1, 2018, the contents of both of which are incorporated herein by reference in their entirety.

FIELD

The present application relates to combination treatments for bacterial infections. For example, the present application relates to the use tulathromycin and gallic acid, for treatment of a *Mannheimia haemolytica* and/or *Pasteurella multocida* bacterial infection or a disease, disorder or condition arising from a *Mannheimia haemolytica* and/or *Pasteurella multocida* bacterial infection. The present application further relates to the use of tulathromycin in combination with gallic acid for treatment of, for example, bovine respiratory disease (BRD).

BACKGROUND

A major relentless global problem of increasing importance is resistance to antimicrobials which is compounded by a dearth of novel antibiotics. Pathogens develop the ability to sense and evade the antimicrobials that render current treatments ineffective. The molecular mechanisms of resistance generally involve mutations in the drug target, or enzymes that directly inactivate the antibiotic and the pumping of antibiotics out of a cell by the activation of efflux pumps. Contributing to resistance development is the indiscriminate use of antibiotics that initiates a selection pressure besides increasing the spectrum of antibiotic exposure to pathogens and transmission of resistance within and between organisms. To this end, combinations of antibiotics have been shown to broaden antimicrobial spectrum and generate synergistic effects. The combination of antibiotics with different mechanisms of action has been used to combat drug resistance as it is less likely that a pathogen will develop resistance to more than one drug simultaneously. Currently available drug-drug combinations exert their activity by the concept of dual synergistic target inhibition wherein two targets (usually in two different pathways) are inhibited concurrently by the two drugs, in effect creating a synergistic effect. Hence, the search for new combinations of antimicrobial compounds has uncovered replacements for existing ineffective antibiotics but microbes eventually developed resistance to them. However, combination therapy has its own disadvantages and irrational use can worsen the already alarming scenario of antibiotic resistance and possibility of adverse effects and superinfection.

One of the most prevalent infectious disease experienced by stockers, producers and feedlot cattle is bovine respiratory disease (BRD). BRD has deleterious effects on cattle health and performance resulting in considerable economic loss. The key pathogenic bacteria for BRD are *Mannheimia hemolytica, Haemophilus somni,* and *Pasteurella multocida* in Canada. Vaccination has shown inconsistent results in terms of protection against BRD pathogens. Tulathromycin was approved for use in Canada for treatment and prevention of BRD in high-risk cattle entering feedlots. Tulathromycin (Draxxin®, Zoetis) is a semi-synthetic macrolide antimicrobial belonging to the subclass of macrolides known as triamilides. Macrolides are bacteriostatic and inhibit essential protein biosynthesis by selectively binding to bacterial ribosomal RNA. They act by stimulating the dissociation of peptidyl-tRNA from the ribosome during the translocation process. Consequently, primary management practices such as metaphylactic antimicrobial injections for BRD prevention are used to reduce the incidences of BRD in feedlot cattle. These practices may contribute to antimicrobial resistance (AMR), which, in turn, will reduce the efficacy of the antimicrobials commonly employed to control infectious disease in cattle. To this end, there is a need to develop an effective treatment protocol for BRD that is efficacious, reduces antimicrobial usage and effectively manages the development of resistance. Also, use of appropriate antibacterial therapy, modulation of the pulmonary inflammatory reaction, and correction of mechanical disorders are therapeutic strategies that minimise the impact of BRD. It has been proposed that irreversible damage to the lung can only be avoided by simultaneous control of bacterial infection and local inflammation (Cattle Practice 15(2):115-119, November 2007). A combination of florfenicol as an antibiotic and a nonsteroidal anti-inflammatory drug (NSAID), such as flunixin has also been proposed.

Plants synthesize a diverse array of secondary metabolites (phytochemicals) that are involved in defense mechanisms and have a wide array of beneficial effects on health and also have antimicrobial properties. The use of antibiotics in combination with natural compounds from plants (phytochemicals) has been reported (1-3). The literature reports suggest that some antibiotic-phytochemical cocktails have the potential to eradicate complex pathogens (3-8). From these studies, there are reasons to believe that plant compounds act as both resistance modifiers and direct inhibitors that act cohesively when combined with antibiotics, increasing their sensitivity to bacterial cells. Also, phytochemicals as antimicrobial agents are relatively safe for use as compared to purely synthetic drugs due to their natural origin, effect against several diseases and drug resistance conditions, and that they are metabolized easily without phytochemical residues being secreted in milk. To add to this, unlike synthetic compounds, natural products and their derivatives mimic or resemble the natural biosynthetic intermediates and endogenous metabolites. Hence, they can be taken up by the cell through active transport systems and show less side-effects (9).

One group of plant secondary metabolites are the phenolic or polyphenol compounds. It is proposed that the antioxidant properties of phenolic acids are conferred by the presence of a benzene ring, a carboxylic acid grouping and one or more hydroxyl and/or methoxyl groupings in the molecule. The metabolite gallic acid is derived from the shikimic acid, an intermediate of secondary metabolism, and is a component of hydrolysable tannins in plants. Gallic acid has been reported to affect the bacterial cell wall of *S. aureus, E. coli,* and *P. aeruginosa,* producing local damage and leakage of cellular materials (10). Gallic acid has been also reported to have synergistic effect with sulfamethoxazole or tetracycline against several *P. aeruginosa* isolates (11) by disruptions of cell wall integrity. In these reports, it also shown that gallic acid in combination with several other antibiotics, including ciprofloxacin, ceftazidime, trimethoprim, tetracyclin, polymyxin B and piperacillin, did not show any synergistic effect against *P. aeruginosa* isolates (11) Further, gallic acid was shown to have a synergistic effect in combination with streptomycin against *E. coli* and *P. aeruginosa* but not *L. monocytogenes* and *S. aureus* (Saavedra, M. J. et al. Medicinal Chemistry, 2010, 6:174-183) This highlights the unpredictability of synergism between plant polyphenols and antibiotics in the inhibition of bacteria, which appears to be organism- and compound-dependent.

The anti-inflammatory potential of gallic acid has been reported in vitro and in vivo (Pharmacological Reports, Volume 69, Issue 4, August 2017, Pages 830-835, Planta Medica 58(6):499-504, January 1993).

SUMMARY

In the present application, the compound gallic acid is disclosed as a potentiator of the macrolide antibiotic, tulathromycin, in the inhibition of the bacteria *Mannheimia haemolytica* and/or *Pasteurella multocida*.

Accordingly, in some embodiments, the present application includes a method of treating or preventing a *Mannheimia haemolytica* and/or *Pasteurella multocida* bacterial infection comprising administering an effective amount of tulathromycin, or a pharmaceutically acceptable salt, prodrug and/or solvate thereof, in combination with an effective amount of gallic acid or a pharmaceutically acceptable salt, prodrug and/or solvate thereof, to a subject in need thereof.

In some embodiments, the present application also includes a method of treating or preventing a disease, disorder or condition arising from a *Mannheimia haemolytica* and/or *Pasteurella multocida* bacterial infection comprising administering an effective amount of tulathromycin, or a pharmaceutically acceptable salt, prodrug and/or solvate thereof, in combination with an effective amount of gallic acid or a pharmaceutically acceptable salt, prodrug and/or solvate thereof, to a subject in need thereof.

In some embodiments, the present application also includes a method of improving the efficacy of tulathromycin for treating a *Mannheimia haemolytica* and/or *Pasteurella multocida* bacterial infection comprising administering an effective amount of tulathromycin, or a pharmaceutically acceptable salt, prodrug and/or solvate thereof, in combination with an effective amount of gallic acid or a pharmaceutically acceptable salt, prodrug and/or solvate thereof, to a subject in need thereof.

In some embodiments, the present application includes a pharmaceutical composition comprising tulathromycin or a pharmaceutically acceptable salt, prodrug and/or solvate thereof, and gallic acid or a pharmaceutically acceptable salt, prodrug and/or solvate thereof wherein the tulathromycin and gallic acid are present in amounts that are effective to treat a *Mannheimia haemolytica* and/or *Pasteurella multocida* bacterial infection, or a disease, disorder or condition arising from a *Mannheimia haemolytica* and/or *Pasteurella multocida* bacterial infection.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

DRAWINGS

The embodiments of the application will now be described in greater detail with reference to the attached drawings in which.

Figure 1A:
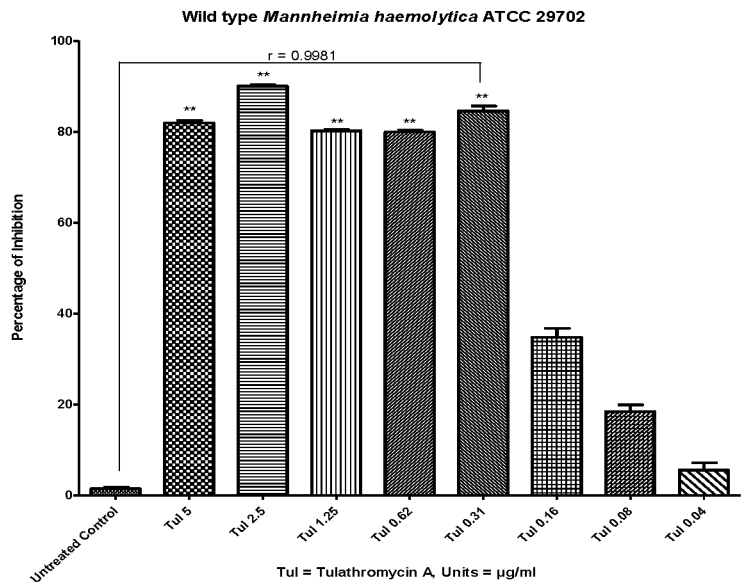
FIG. 1A is a bar graph for the determination of the minimum inhibitory concentration of tulathromycin (Tul) for *M. haemolytica*.

FIG. 4A is a bar graph showing the antibacterial activity of gallic acid at sub-minimum inhibitory concentration doses (250, 125, 62.5, 31.25, 15.6, 7.8 and 3.9 µg/ml) and tulathromycin at sub-minimum inhibitory concentration doses (5, 2.5, 1.25, 0.62, 0.31, 0.16, 0.08 and 0.04) and the antibacterial activity of various doses of gallic acid combination with various doses of tulathromycin for inhibition of *M. haemolytica* in exemplary embodiments of the application.

FIG. 4B is a bar graph showing the antibacterial activity of gallic acid at sub-minimum inhibitory concentration doses (500, 250, 125, 62.5, 31.25, 15.6, 7.8 and 3.9 µg/ml] and tulathromycin at sub-minimum inhibitory concentration doses [5, 2.5, 1.25, 0.62, 0.31, 0.16, 0.08 and 0.04] and the antibacterial activity of various doses of gallic acid combination with various doses of tulathromycin for inhibition of *P. multocida* in exemplary embodiments of the application.

FIG. 5A is a bar graph showing that *M. haemolytica* treated with sub-minimum inhibitory concentration doses of tulathromycin under stress generation conditions looses its sensitivity to tulathromycin producing 17.16% resistance at 0.62 µg/ml.

FIG. 5B is a bar graph showing that *M. haemolytica* treated with sub-minimum inhibitory concentration doses of gallic acid under stress generation conditions has no effect on the sensitivity of the bacteria.

FIG. 6A is a bar graph showing that *P. multocida* treated with sub-minimum inhibitory concentration doses of tulathromycin under stress generation conditions has no effect on the sensitivity of the bacteria.

FIG. 6B is a bar graph showing that *P. multocida* treated with sub-minimum inhibitory concentration doses of gallic acid under stress generation conditions has no effect on the sensitivity of the bacteria.

DETAILED DESCRIPTION

I. Definitions

Unless otherwise indicated, the definitions and embodiments described in this and other sections are intended to be applicable to all embodiments and aspects of the present application herein described for which they are suitable as would be understood by a person skilled in the art.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

The term "consisting" and its derivatives, as used herein, are intended to be closed terms that specify the presence of the stated features, elements, components, groups, integers, and/or steps, but exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise.

In embodiments comprising an "additional" or "second" component, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present.

The term "bacterial infection" as used herein refers to an invasion of cells or bodily tissues by one or more foreign, undesirable bacteria.

The term "phytochemical" as used herein refers to a biologically active compound produced by plants.

The term "antibiotic" as used herein refers to an antimicrobial drug used in the treatment and prevention of bacterial infections.

The term "gallic acid" refers to a compound of the Formula:

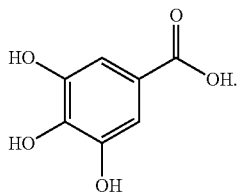 [SMILES: O=C(O)c1cc(O)c(O)c(O)c1]

The term "tulathromycin" as used herein refers to a compound having the IUPAC name: (2R,3S,4R,5R,8R,10R,11R,12S,13S,14R)-13-[[2,6-dideoxy-3-C-methyl-3-O-methyl-4-C-[(propylamino)methyl]-a-L-ribo-hexopyranosyl]oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-6-azacyclopentadecan-15-one, also known as CP 472,295 and having the chemical Formula:

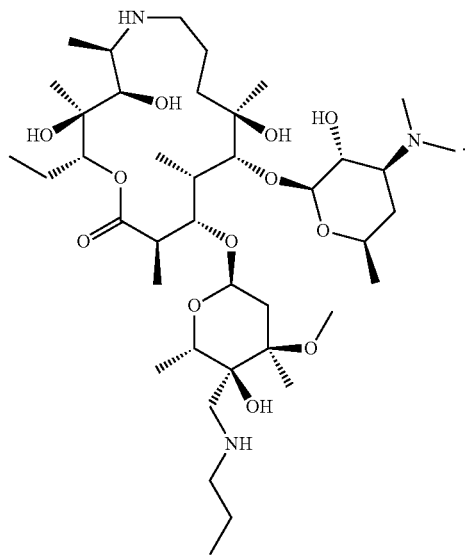 [SMILES: CCCNC[C@]1(O)[C@H](C)O[C@@H](O[C@H]2[C@H](C)[C@@H](O[C@@H]3O[C@H](C)C[C@H](N(C)C)[C@H]3O)[C@](C)(O)CCCN[C@H](C)[C@@H](O)[C@](C)(O)[C@@H](CC)OC(=O)[C@@H]2C)C[C@@]1(C)OC]

The term "pharmaceutically acceptable salt" means an acid addition salt or a basic addition salt suitable for, or compatible with, the treatment of subjects.

The term "pharmaceutically acceptable salts" embraces salts commonly used to form addition salts of free acids or free bases.

The term "solvates" as used herein refers to complexes formed between a compound and a solvent from which the compound is precipitated or in which the compound is made. Accordingly, the term "solvate" as used herein means a compound, or a salt and/or prodrug of a compound, wherein molecules of a suitable solvent are incorporated in the crystal lattice.

The term "prodrug" as used herein refers to, for example, conventional esters formed with available hydroxy, thiol, amino or carboxyl groups.

The expression "disease, disorder or condition arising from a bacterial infection" as used herein refers to any disease, disorder or condition that is directly or indirectly caused by the presence of a bacterial infection in a subject.

The term "subject" as used herein includes all members of the animal kingdom including mammals.

The term "pharmaceutical composition" as used herein refers to a composition of matter for pharmaceutical use.

The term "pharmaceutically acceptable" means compatible with the treatment of subjects, for example, mammals such as bovines, equines and humans.

The term "parenteral" as used herein means taken into the body or administered in a manner other than through the gastrointestinal tract.

The term "administered" as used herein means administration of an effective amount of a compound to a cell either in cell culture or in a subject.

As used herein, the term "effective amount" or "therapeutically effective amount" means an amount effective, at dosages and for periods of time necessary to achieve a desired result.

The terms "to treat", "treating" and "treatment" as used herein and as is well understood in the art, means an approach for obtaining beneficial or desired results, including clinical results. Beneficial or desired clinical results include, but are not limited to, diminishment of extent of bacterial infection, stabilization (i.e. not worsening) of the state of the bacterial infection, preventing spread of the bacterial infection, delay or slowing of infection progression, amelioration or palliation of the bacterial infectious state, diminishment of the reoccurrence of bacterial infection, diminishment, stabilization, alleviation or amelioration of one or more diseases, disorders or conditions arising from the bacterial infection, diminishment of the reoccurrence of one or more diseases, disorders or conditions arising from the bacterial infection, and remission of the bacterial infection and/or one or more symptoms or conditions arising from the bacterial infection, whether partial or total, whether detectable or undetectable. "To treat", "treating" and "treatment" can also mean prolonging survival as compared to expected survival if not receiving treatment. "To treat", "treating" and "treatment" as used herein also include prophylactic treatment. For example, a subject with an early bacterial infection is treated to prevent progression, or alternatively a subject in remission is treated to prevent recurrence.

"Palliating" an infection, disease, disorder and/or condition means that the extent and/or undesirable clinical manifestations of an infection, disease, disorder and/or condition are lessened and/or time course of the progression is slowed or lengthened, as compared to not treating the infection, disease, disorder and/or condition.

The term "prevention" or "prophylaxis" and the like as used herein refers to a reduction in the risk or probability of a subject becoming afflicted with a bacterial infection and/or a disease, disorder and/or condition arising from a bacterial infection or manifesting a symptom associated with a bacterial infection and/or a disease, disorder and/or condition arising from a bacterial infection.

When used, for example, with respect to the methods of treatment, uses, compositions and kits of the application, a subject, for example a subject "in need thereof" is a subject who has been diagnosed with, is suspected of having, may come in to contact with, and/or was previously treated for a bacterial infection or a disease, disorder or condition arising from a bacterial infection.

II. Treatment Methods and Uses of the Application

The present application includes a method of treating or preventing a *Mannheimia haemolytica* and/or *Pasteurella multocida* bacterial infection in a subject comprising administering, to a subject in need thereof, an effective amount of gallic acid, or a pharmaceutically acceptable salt, prodrug and/or solvate thereof, in combination with an effective amount of tulathromycin or a pharmaceutically acceptable salt, prodrug and/or solvate thereof.

The present application also includes a use of gallic acid, or a pharmaceutically acceptable salt, prodrug and/or solvate thereof, in combination with an effective amount of tulathromycin or a pharmaceutically acceptable salt, prodrug and/or solvate thereof, for treating a *Mannheimia haemolytica* and/or *Pasteurella multocida* bacterial infection in a subject; a use of gallic acid, or a pharmaceutically acceptable salt, prodrug and/or solvate thereof, in combination with tulathromycin or a pharmaceutically acceptable salt, prodrug and/or solvate thereof, for preparation of a medicament for treating a *Mannheimia haemolytica* and/or *Pasteurella multocida* bacterial infection in a subject; and gallic acid, or a pharmaceutically acceptable salt, prodrug and/or solvate thereof, in combination with tulathromycin or a pharmaceutically acceptable salt, prodrug and/or solvate thereof, for use to treat a *Mannheimia haemolytica* and/or *Pasteurella multocida* bacterial infection in a subject.

In another embodiment, the present application includes a method of treating or preventing a disease, disorder or condition arising from a *Mannheimia haemolytica* and/or *Pasteurella multocida* bacterial infection in a subject comprising administering, to a subject in need thereof, an effective amount of gallic acid, or a pharmaceutically acceptable salt, prodrug and/or solvate thereof, in combination with an effective amount of tulathromycin or a pharmaceutically acceptable salt, prodrug and/or solvate thereof.

The present application also includes a use of gallic acid, or a pharmaceutically acceptable salt, prodrug and/or solvate thereof, in combination with tulathromycin or a pharmaceutically acceptable salt, prodrug and/or solvate thereof, for treating a disease, disorder or condition arising from a *Mannheimia haemolytica* and/or *Pasteurella multocida* bacterial infection in a subject; a use of gallic acid, or a pharmaceutically acceptable salt, prodrug and/or solvate thereof, in combination with tulathromycin or a pharmaceutically acceptable salt, prodrug and/or solvate thereof, for preparation of a medicament for treating a disease, disorder or condition arising from a *Mannheimia haemolytica* and/or *Pasteurella multocida* bacterial infection in a subject; and the use of gallic acid, or a pharmaceutically acceptable salt, prodrug and/or solvate thereof, in combination with tulathromycin or a pharmaceutically acceptable salt, prodrug and/or solvate thereof, for use to treat a disease, disorder or condition arising from a *Mannheimia haemolytica* and/or *Pasteurella multocida* bacterial infection in a subject.

In another embodiment, the present application includes a method of improving the efficacy of tulathromycin for treating a *Mannheimia haemolytica* and/or *Pasteurella multocida* bacterial infection comprising administering an effective amount of gallic acid, or a pharmaceutically acceptable salt, prodrug and/or solvate thereof, in combination with an effective amount of tulathromycin or a pharmaceutically acceptable salt, prodrug and/or solvate thereof to a subject in need thereof.

The present application also includes a use of gallic acid, or a pharmaceutically acceptable salt, prodrug and/or solvate thereof, in combination with tulathromycin or a pharmaceutically acceptable salt, prodrug and/or solvate thereof, for improving the efficacy of tulathromycin for treating a disease, disorder or condition arising from a *Mannheimia haemolytica* and/or *Pasteurella multocida* bacterial infection in a subject; a use of gallic acid, or a pharmaceutically acceptable salt, prodrug and/or solvate thereof, in combination with tulathromycin or a pharmaceutically acceptable salt, prodrug and/or solvate thereof, for the preparation of a medicament for improving the efficacy of tulathromycin for treating a *Mannheimia haemolytica* and/or *Pasteurella multocida* bacterial infection in a subject; and the use of gallic acid, or a pharmaceutically acceptable salt, prodrug and/or solvate thereof, in combination with tulathromycin or a pharmaceutically acceptable salt, prodrug and/or solvate thereof, for use to improve the efficacy of tulathromycin for treating a *Mannheimia haemolytica* and/or *Pasteurella multocida* bacterial infection in a subject.

In another embodiment, the present application includes a method of improving the efficacy of tulathromycin for treating a disease, disorder or condition arising from a *Mannheimia haemolytica* and/or *Pasteurella multocida* bacterial infection comprising administering an effective amount of gallic acid, or a pharmaceutically acceptable salt, prodrug and/or solvate thereof, in combination with an effective amount of tulathroymicin or a pharmaceutically acceptable salt, prodrug and/or solvate thereof, to a subject in need thereof.

The present application also includes a use of gallic acid, or a pharmaceutically acceptable salt, prodrug and/or solvate thereof, in combination with tulathromycin or a pharmaceutically acceptable salt, prodrug and/or solvate thereof, for improving the efficacy of tulathromycin for treating a disease, disorder or condition arising from from a *Mannheimia haemolytica* and/or *Pasteurella multocida* bacterial infection in a subject; a use of gallic acid, or a pharmaceutically acceptable salt, prodrug and/or solvate thereof, in combination with tulathromycin or a pharmaceutically acceptable salt, prodrug and/or solvate thereof, for the preparation of a medicament for improving the efficacy of tulathromycin for treating a disease, disorder or condition arising from *Mannheimia haemolytica* and/or *Pasteurella multocida* bacterial infection in a subject; and the use of gallic acid, or a pharmaceutically acceptable salt, prodrug and/or solvate thereof, in combination with tulathromycin or a pharmaceutically acceptable salt, prodrug and/or solvate thereof, for use to improve the efficacy of tulathromycin for treating a disease, disorder or condition arising from *Mannheimia haemolytica* and/or *Pasteurella multocida* bacterial infection in a subject.

In some embodiments, the bacterial infection is an infection of at least one bacterium belonging to the species *Mannheimia hemolytica*.

In some embodiments, the bacterial infection is an infection of at least one bacterium belonging to the species *Pasteurella multocida*.

In some embodiments, the bacterial infection is an infection of at least one bacterium belonging to the species *Mannheimia hemolytica* and at least one bacterium belonging to the species *Pasteurella multocida*.

In some embodiments, the disease, disorder or condition arising from *Mannheimia haemolytica* and/or *Pasteurella multocida* bacterial infection is selected from one or more of bovine respiratory disease (BRD), bovine mastitis, shipping fever, and other bovine pasteurellosis conditions.

Tulathromycin and gallic acid are both available from commercial sources or can be prepared using methods known in the art.

In some embodiments, suitable pharmaceutically acceptable acid addition salts are prepared from an inorganic acid or an organic acid. Examples of such inorganic acids include, without limitation, hydrochloric, hydrobromic, hydroiodic, nitric, carbonic, sulfuric and phosphoric acid. Examples of appropriate organic acids include, for example, aliphatic, cycloaliphatic, aromatic, arylaliphatic, heterocyclic, carboxylic and sulfonic classes of organic acids, examples of which include, without limitation, formic, acetic, propionic, succinic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactic, and galacturonic acid.

In some embodiments, suitable pharmaceutically-acceptable base addition salts include, but are not limited to, metallic salts made from aluminum, calcium, lithium, magnesium, potassium, sodium and zinc or organic salts made from N,N'-dibenzylethylenediamine, chloroprocaine, choline, diethanolamine, ethylenediamine, N-methylglucamine, lysine and procaine.

Formation of a pharmaceutically-acceptable salt may be achieved using standard techniques. For example, a neutral compound is treated with an acid or base in a suitable solvent and the formed salt is isolated by filtration, extraction or any other suitable method.

Examples of suitable solvate solvents are ethanol, water and the like. When water is the solvent, the molecule is referred to as a "hydrate". The formation of solvates will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art.

Various forms, including crystal forms and salts, of tulathromycin are described, for example, in WO 2013/013834, EP2402355 and WO 2011/149749, the contents of which are incorporated herein by reference.

Various crystal forms and salts of gallic acid are described, for example, in Braun D et al. Crystal Growth & Design, 13, pages 19-23 2013 and Clarke D. et al. Crystal Growth & Design, 11 (4) p 964-966 2011, and Nayeem et al. J. Applied Pharmacy, 8:2 2016, the contents of which are incorporated herein by reference.

Prodrugs of the compounds (gallic acid and/or tulathromycin, or salts and/or solvates thereof), may be prepared, for example, by acylating available hydroxy or amino groups using an activated acid in the presence of a base, and optionally, in inert solvent (e.g. an acid chloride in pyridine). Similarly, available carboxylic acid groups may be converted to ester groups using known chemistry, for example, by activation in the presence of base and reaction with suitable groups containing a nucleophile. Some common esters which have been utilized as prodrugs are phenyl esters, aliphatic ($C_1$-$C_{24}$) esters, acyloxymethyl esters, carbamates and amino acid esters.

In the context of treating a bacterial infection, or a disease, disorder or condition arising from a bacterial infection, an effective amount of the tulathromycin, or a salt, prodrug and/or solvate thereof or gallic acid or a salt, prodrug and/or solvate thereof, is an amount that, for example, reduces the bacterial infection compared to the bacterial infection without administration of tulathromycin or a salt, prodrug and/or solvate thereof and gallic acid, or a salt, prodrug and/or solvate thereof. Further, in the context of improving the efficacy of an antibiotic for the treatment of a bacterial infection or a disease, disorder or condition arising from a bacterial infection an effective amount gallic acid, or a salt, prodrug and/or solvate thereof, is, for example, an amount that, for example, reduces the bacterial infection compared to the reduction of the bacterial infection with administration of the antibiotic alone. By "reducing the infection", it is meant, for example, reducing the amount of the infectious agent in the subject and/or reducing the symptoms of the infection. Effective amounts may vary according to factors such as the disease state, age, sex and/or weight of the subject. The amount of a given compound or composition that will correspond to such an amount will vary depending upon various factors, such as the given compound or composition, the pharmaceutical formulation, the route of administration, the type of condition, disease or disorder, the identity of the subject being treated, and the like, but can nevertheless be routinely determined by one skilled in the art.

The antibiotic is administered to a subject, or used, in a variety of forms depending on the selected route of administration, as will be understood by those skilled in the art. In some embodiments, the antibiotic is administered to the subject, or used, by oral (including sublingual and buccal) or parenteral (including, intravenous, intraperitoneal, subcutaneous, intramuscular, transepithelial, nasal, intrapulmonary, intrathecal, rectal, topical, patch, pump and transdermal) administration and the antibiotic formulated accordingly. Conventional procedures and ingredients for the selection and preparation of suitable compositions are described, for example, in Remington's Pharmaceutical Sciences (2000-20th edition) and in The United States Pharmacopeia: The National Formulary (USP 24 NF19) published in 1999. In general, the antibiotic is used in the form in which is it available and administered to subjects. Such forms, include, for example in the form of their pharmaceutically acceptable salts, in the form of fine particles of the zwitterionic form and in an injectable or infusable suspensions.

Gallic acid or a pharmaceutically acceptable salt, prodrug and/or solvate thereof, is also administered to a subject, or used, in a variety of forms depending on the selected route of administration, as will be understood by those skilled in the art. In some embodiments, gallic acid is administered to the subject, or used, by oral (including sublingual and buccal) or parenteral (including, intravenous, intraperitoneal, subcutaneous, intramuscular, transepithelial, nasal, intrapulmonary, intrathecal, rectal, topical, patch, pump and transdermal) administration and the compound, salt and/or solvate, formulated accordingly. Again, conventional procedures and ingredients for the selection and preparation of suitable compositions are described, for example, in Remington's Pharmaceutical Sciences (2000-20th edition) and in The United States Pharmacopeia: The National Formulary (USP 24 NF19) published in 1999.

The pharmaceutical forms suitable for injectable use include sterile aqueous solutions or dispersions and sterile powders for the extemporaneous preparation of sterile injectable solutions or dispersions. In all cases, the form is sterile and fluid to the extent that easy syringability exists.

In some embodiments, parenteral administration is by continuous infusion over a selected period of time. Solutions suitable for parenteral administration are prepared by known methods by a person skilled in the art. For example, tulathromycin or a salt, prodrug and/or solvate thereof, or gallic acid, or a salt, prodrug and/or solvate thereof, is prepared in water optionally mixed with a surfactant such as hydroxypropylcellulose. Dispersions are also prepared in glycerol, liquid polyethylene glycols, DMSO and mixtures thereof with or without alcohol, and in oils. Under ordinary conditions of storage and use, these preparations contain a preservative to prevent the growth of microorganisms.

Compositions for nasal administration are conveniently formulated as aerosols, drops, gels or powders. Aerosol formulations typically comprise a solution or fine suspension of the active substance in a physiologically acceptable aqueous or non-aqueous solvent and are usually presented in single or multidose quantities in sterile form in a sealed container, which take the form of a cartridge or refill for use with an atomising device. Alternatively, the sealed container is a unitary dispensing device such as a single dose nasal inhaler or an aerosol dispenser fitted with a metering valve which is intended for disposal after use. Where the dosage form comprises an aerosol dispenser, it contains a propellant which is, for example, a compressed gas such as compressed air or an organic propellant such as fluorochlorohydrocarbon. In some embodiments, the aerosol dosage forms take the form of a pump-atomizer.

Compositions suitable for buccal or sublingual administration include tablets, lozenges, and pastilles, wherein the active ingredient is formulated with a carrier such as sugar, acacia, tragacanth, gelatin and/or glycerine. Compositions for rectal administration are conveniently in the form of suppositories containing a conventional suppository base such as cocoa butter.

In another embodiment, tulathromycin or a salt, prodrug and/or solvate thereof, or gallic acid, or a salt, prodrug and/or solvate thereof, is orally administered, for example, with an inert diluent or with an assimilable edible carrier, or it is enclosed in hard or soft shell gelatin capsules, or it is compressed into tablets, or it is incorporated directly with the food of a diet. For oral administration, tulathromycin or gallic acid, or a salt, prodrug and/or solvate thereof, is incorporated with excipients and used in the form of, for example, ingestible tablets, buccal tablets, troches, capsules, elixirs, suspensions, syrups, wafers, and the like. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., molecular sieving type particles, or, a fine hollow permeable fiber bundle, or chopped hollow permeable fibers, agglomerated or held in a fibrous packet. In some embodiments, timed-release compositions are, formulated, as liposomes or those wherein the active compound is protected with differentially degradable coatings, such as by microencapsulation, multiple coatings, etc. Liposome delivery systems include, for example, small unilamellar vesicles, large unilamellar vesicles and multilamellar vesicles. In some embodiments, liposomes are formed from a variety of lipids, such as cholesterol, stearylamine or phosphatidylcholines.

It is also possible to freeze-dry tulathromycin or a salt, prodrug and/or solvate thereof, or gallic acid, or a salt, prodrug and/or solvate thereof, and use the lyophilizate obtained, for example, for the preparation of products for injection.

In some embodiments, tulathromycin or a salt, prodrug and/or solvate thereof, or gallic acid, or a salt, prodrug and/or solvate thereof, is coupled with soluble polymers as targetable drug carriers. Such polymers include, for example, polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. In a further embodiment, tulathromycin or a salt, prodrug and/or solvate thereof, or gallic acid, or a salt, prodrug and/or solvate thereof, is coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

Tulathromycin or a salt, prodrug and/or solvate thereof, or gallic acid, or a salt, prodrug and/or solvate thereof, are used in combination with each other. tulathromycin or a salt, prodrug and/or solvate thereof, or gallic acid, or a salt, prodrug and/or solvate thereof, are either used or administered separately in time and/or in mode of administration (i.e. different administration routes) or they are administered together in the same pharmaceutical preparation.

In one embodiment tulathromycin or a salt, prodrug and/or solvate thereof, or gallic acid, or a salt, prodrug and/or solvate thereof, are used or administered separately in time and/or in mode of administration. For example, tulathromycin or a salt, prodrug and/or solvate thereof, is administered by injection and gallic acid, or a salt, prodrug and/or solvate thereof, is administered orally. In another example, tulathromycin, or a salt, prodrug and/or solvate thereof, is administered orally and gallic acid, or a salt, prodrug and/or solvate thereof, is administered by injection. In a further example, both tulathromycin, or a salt, prodrug and/or solvate thereof, and gallic acid, or a salt, prodrug and/or solvate thereof, are administered orally or by injection. When tulathromycin, or a salt, prodrug and/or solvate thereof, and gallic acid, or a salt, prodrug and/or solvate thereof, are used or administered separately in time and/or in mode of administration, tulathromycin, or a salt, prodrug and/or solvate thereof, is administered, or used, either before or after administration, or use, of gallic acid, or a salt, prodrug and/or solvate thereof.

In another embodiment, tulathromycin, or a salt, prodrug and/or solvate thereof, and gallic acid, or a salt, prodrug and/or solvate thereof, are administered contemporaneously. As used herein, "contemporaneous administration" of two substances to a subject means providing tulathromycin, or a salt, prodrug and/or solvate thereof, and gallic acid, or a salt, prodrug and/or solvate thereof, so that they are both biologically active in the subject at the same time. The exact details of the administration will depend on the pharmacokinetics of tulathromycin, or a salt, prodrug and/or solvate thereof, and gallic acid, or a salt, prodrug and/or solvate thereof, in the presence of each other, and can include administering tulathromycin, or a salt, prodrug and/or solvate thereof, and gallic acid, or a salt, prodrug and/or solvate thereof, within a few hours of each other, or even administering tulathromycin, or a salt, prodrug and/or solvate thereof, and gallic acid, or a salt, prodrug and/or solvate thereof, within 24 hours or greater of administration of the other, if the pharmacokinetics are suitable. Design of suitable dosing regimens is routine for one skilled in the art.

In some embodiments, tulathromycin, or a salt, prodrug and/or solvate thereof, and gallic acid or a salt, prodrug and/or solvate thereof, are administered to a subject in a single composition or formulation.

In another embodiment of the present application, tulathromycin, or a salt, prodrug and/or solvate thereof, and gallic acid, or a salt, prodrug and/or solvate thereof, are administered to a subject in a non-contemporaneous fashion.

In a further embodiment of the present application, tulathromycin, or a salt, prodrug and/or solvate thereof, and gallic acid, or a salt, prodrug and/or solvate thereof, are administered to the subject in a contemporaneous fashion followed by, or alternating with, administration in a non-contemporaneous fashion.

Treatment methods comprise administering to a subject tulathromycin, or a salt, prodrug and/or solvate thereof, and gallic acid, or a salt, prodrug and/or solvate thereof, and optionally consists of a single administration, or alternatively comprises a series of administrations. The length of the treatment period depends on a variety of factors, such as the severity of the disease, disorder or condition, the age of the subject, the dosage of tulathromycin, or a salt, prodrug and/or solvate thereof, and gallic acid, or a salt, prodrug and/or solvate thereof, the activity of tulathromycin, or a salt, prodrug and/or solvate thereof, and gallic acid, or a salt, prodrug and/or solvate thereof, and/or a combination thereof.

It is an embodiment that tulathromycin, or a salt, prodrug and/or solvate thereof, is administered or used according to treatment protocol that is known for the antibiotic in the treatment of bacterial infections.

In some embodiments, tulathromycin, or a salt, prodrug and/or solvate thereof, and gallic acid, or a salt, prodrug and/or solvate thereof, are administered or used as soon as possible after exposure to the bacteria. In some embodiments, tulathromycin, or a salt, prodrug and/or solvate thereof, and gallic acid, or a salt, prodrug and/or solvate thereof, are administered or used until treatment of the bacterial infection is achieved. For example, until complete elimination of the bacteria is achieved, or until the number of bacteria has been reduced to the point where the subject's defenses are no longer overwhelmed and can kill any remaining bacteria.

The dosage of the tulathromycin, or a salt, prodrug and/or solvate thereof, and gallic acid, or a salt, prodrug and/or solvate thereof, varies depending on many factors such as the pharmacodynamic properties thereof, the mode of administration, the age, health and weight of the subject, the nature and extent of the symptoms, the frequency of the treatment and the type of concurrent treatment, if any, and the clearance rate in the subject to be treated. One of skill in the art can determine the appropriate dosage based on the above factors. tulathromycin, or a salt, prodrug and/or solvate thereof, and gallic acid, or a salt, prodrug and/or solvate thereof, may be administered initially in a suitable dosage that may be adjusted as required, depending on the clinical response.

In some embodiments, the dosage of tulathromycin, or a salt, prodrug and/or solvate thereof, is equal to or less than the dosage of such agents when used alone. Such dosages are known to or readily determined by those skilled in the art.

III. Compositions and Kits of the Application

The present application also includes a pharmaceutical composition comprising tulathromycin or a pharmaceutically acceptable salt, prodrug and/or solvate thereof and gallic acid or a pharmaceutically acceptable salt, prodrug and/or solvate thereof wherein the gallic acid and tulathromycin are present in amounts that are effective to treat a *Mannheimia haemolytica* and/or *Pasteurella multocida* bacterial infection or a disease, disorder or condition arising from a *Mannheimia haemolytica* and/or *Pasteurella multocida* bacterial infection.

The present application also includes a pharmaceutical composition comprising tulathromycin or a pharmaceutically acceptable salt, prodrug and/or solvate thereof and gallic acid or a pharmaceutically acceptable salt, prodrug and/or solvate thereof wherein the gallic acid and tulathromycin are present in amounts that are effective for improving the efficacy of tulathromycin to treat a *Mannheimia haemolytica* and/or *Pasteurella multocida* bacterial infection or a disease, disorder or condition arising from a *Mannheimia haemolytica* and/or *Pasteurella multocida*. In some embodiments, the disease, disorder or condition arising from *Mannheimia haemolytica* and/or *Pasteurella multocida* bacterial infection is selected from one or more of bovine respiratory disease (BRD), bovine mastitis, shipping fever, and other bovine pasteurellosis conditions.

The present application also includes a kit for the treatment of a *Mannheimia haemolytica* and/or *Pasteurella multocida* bacterial infection or a disease, disorder or condition arising from a *Mannheimia haemolytica* and/or *Pasteurella multocida* bacterial infection, the kit comprising tulathromycin or a pharmaceutically acceptable salt, prodrug and/or solvate thereof and gallic acid or a pharmaceutically acceptable salt, prodrug and/or solvate thereof and optionally instructions for administration of tulathromycin and gallic acid, or a pharmaceutically acceptable salt and/or solvate thereof, to a subject in need thereof.

The present application also includes a kit for the treatment of a bacterial infection, or a disease, disorder or condition arising from a *Mannheimia haemolytica* and/or *Pasteurella multocida* bacterial infection, the kit comprising: gallic acid or a pharmaceutically acceptable salt and/or solvate thereof; and instructions for administration of gallic acid, or a pharmaceutically acceptable salt and/or solvate thereof, to a subject being administered tulathromycin for a bacterial infection or a disease, disorder or condition arising from a *Mannheimia haemolytica* and/or *Pasteurella multocida* bacterial infection.

The present application also includes a kit for improving the efficacy of tulathromycin for the treatment of a *Mannheimia haemolytica* and/or *Pasteurella multocida* bacterial infection or a disease, disorder or condition arising from a *Mannheimia haemolytica* and/or *Pasteurella multocida* bacterial infection, the kit comprising tulathromycin or a pharmaceutically acceptable salt, prodrug and/or solvate thereof and gallic acid or a pharmaceutically acceptable salt, prodrug and/or solvate thereof; and optionally instructions for administration of the tulathromycin or a pharmaceutically acceptable salt, prodrug and/or solvate thereof and gallic acid or a pharmaceutically acceptable salt, prodrug and/or solvate thereof, to a subject in need thereof.

The present application also includes a kit for improving the efficacy of tulathromycin for the treatment of a *Mannheimia haemolytica* and/or *Pasteurella multocida* bacterial infection, or a disease, disorder or condition arising from a *Mannheimia haemolytica* and/or *Pasteurella multocida* bacterial infection, the kit comprising gallic acid, or a pharmaceutically acceptable salt and/or solvate thereof; and instructions for administration gallic acid, or a pharmaceutically acceptable salt and/or solvate thereof, to a subject being administered tulathromycin for the treatment of a *Mannheimia haemolytica* and/or *Pasteurella multocida* bacterial infection or a disease, disorder or condition arising from a *Mannheimia haemolytica* and/or *Pasteurella multocida* bacterial infection.

In some embodiments, tulathromycin or a pharmaceutically acceptable salt, prodrug and/or solvate thereof and gallic acid or a pharmaceutically acceptable salt, prodrug and/or solvate thereof, in the compositions and kits of the present application are formulated as separate pharmaceutical compositions, for separate administration to, or use in, subjects. In this embodiment, the separate pharmaceutical compositions are formulated independently of each other and in accordance with the desired mode of administration for each active.

In some embodiments, tulathromycin or a pharmaceutically acceptable salt and/or solvate thereof is formulated for administration, or use, by oral delivery or for delivery by injection. In another embodiment, gallic acid, or a pharmaceutically acceptable salt and/or solvate thereof is formulated for administration, or use, by oral delivery or for delivery by injection.

In some embodiments, gallic acid, or a pharmaceutically acceptable salt and/or solvate thereof, and the tulathromycin or a pharmaceutically acceptable salt and/or solvate thereof in the compositions and kits of the present application are formulated as a single pharmaceutical composition, for combined, simultaneous administration to, or use in, subjects. In some embodiments, the single pharmaceutical composition is formulated for administration, or use, by oral delivery or by injection.

The following non-limiting examples are illustrative of the present application:

EXAMPLES

Example 1

Materials and Methods
(a) Antibiotics and Excipients

Gallic acid was obtained from Alfa Aesar. tulathromycin was obtained from the Cayman chemical company.
(b) Bacterial Strains and Media The bacterial strains of *Mannheimia haemolytica* ATCC 29702 and *Pasteurella multocida* ATCC 43137 were purchased from American Type Culture Collection (ATCC) distributor CEDARLANE Corporation, Burlington, Ontario, Canada and revived according to the manufacturer's instruction. Bacteria were grown in Brain Heart Infusion broth (BHIB).
(c) Determination of Minimum Inhibitory Concentration (MIC)

MIC of tulathromycin and gallic acid against *Mannheimia haemolytica* and *Pasteurella multocida* was determined by using standard broth micro dilution assay as outlined by CLSI (Richard S, Lynn S-M, Avery C G. Antimicrobial susceptibility testing protocols. New York: CRC Press; 2007). Strains were sub-cultured in Brain Heart Infusion Broth (BHIB), incubated at 37° C. overnight and bacterial suspension OD was adjusted with the media to 0.5 McFarland turbidity as per CLSI protocol (Approx. cell density $1.5 \times 10^8$ CFU/mL) using normal saline as control. 100 µl of broth was added to each well (including positive control wells) and then serial dilution of tulathromycin (5 to 0.04 µg/ml) and gallic acid (500 to 3.9 µg/ml) was executed. 5 µl of bacterial sample was added to all the wells except the positive control well. Negative controls were validated by taking bacterial suspension from the well and plated on Columbia agar with 5% sheep blood (Oxoid MP0351) to confirm purity and growth. Plates were then incubated at 37° C. for 18-24 h and were subsequently read automatically by using 96 well plate reader (BIORAD iMark Microplate Reader) at 655 nm. The readings were double checked manually using the Sensititre Vizion System.
(d) MIC against the Coculture of *M. haemolytica* and *P. multocida*

MIC of tulathromycin, gallic acid and its combinations were determined against the co-culture of *M. haemolytica* and *P. multocida*. The overnight grown cultures of *M. haemolytica* and *P. multocida* were adjusted to 0.5 McFarland standard turbidity in BHIB, and then equal proportion of each of the cultures was added in the 96 well plates. After the addition of serially diluted drugs, the plates were incubated at 37° C. overnight and read as of above.
(e) Resistance Generation For the resistance generation studies, *M. haemolytica* and *P. multocida* were cultured in the presence of sub-MIC doses (1/2 MIC) of tulathromycin and gallic acid individually until they reach 1 unit OD at 565 nm. The bacterial cells were then given antibiotic stress relaxation by culturing them in BHIB till 1 OD unit of turbidity is reached at 565 nm. This first pass cycle of culturing in sub-MIC dose of tulathromycin, and relaxing in BHIB is considered as 1st generation (1G-TulathromycinA). The cycle as above was repeated to obtain $2^{nd}$ and $3^{rd}$ generation of bacterial cultures. Subsequently, MIC assays were performed with all the three generations of the two bacterial strains to evaluate the level of sensitivity towards tulathromycin. The experiments were repeated with gallic acid.

(f) Synergy Studies

For the drug interaction studies, gallic acid was mixed with tulathromycin to test the drug interactions between tulathromycin and gallic acid. This was done by a checker board serial dilution technique performed in 96-well polypropylene plates (as explained elsewhere, for example, in [11]). The fractional inhibitory concentration (FIC) index of the combinations of antimicrobial compounds was calculated according to the equation:

$$\text{FIC index} = \text{FIC}_A + \text{FIC}_B = A/\text{MIC}_A + B/\text{MIC}_B$$

where A (gallic acid) and B (Tulathromycin) are the MICs of compound A and compound B in combination. $\text{MIC}_A$ and $\text{MIC}_B$ are the MICs of compound A and compound B, separately, $\text{FIC}_A$ and $\text{FIC}_B$ are the FICs of compound A and compound B (Hal M J J Antimicrob Chemother. 1983 May; 11(5):427-33).

Results (a) Antimicrobial Activity of Tulathromycin and Gallic Acid

Figure 1B:
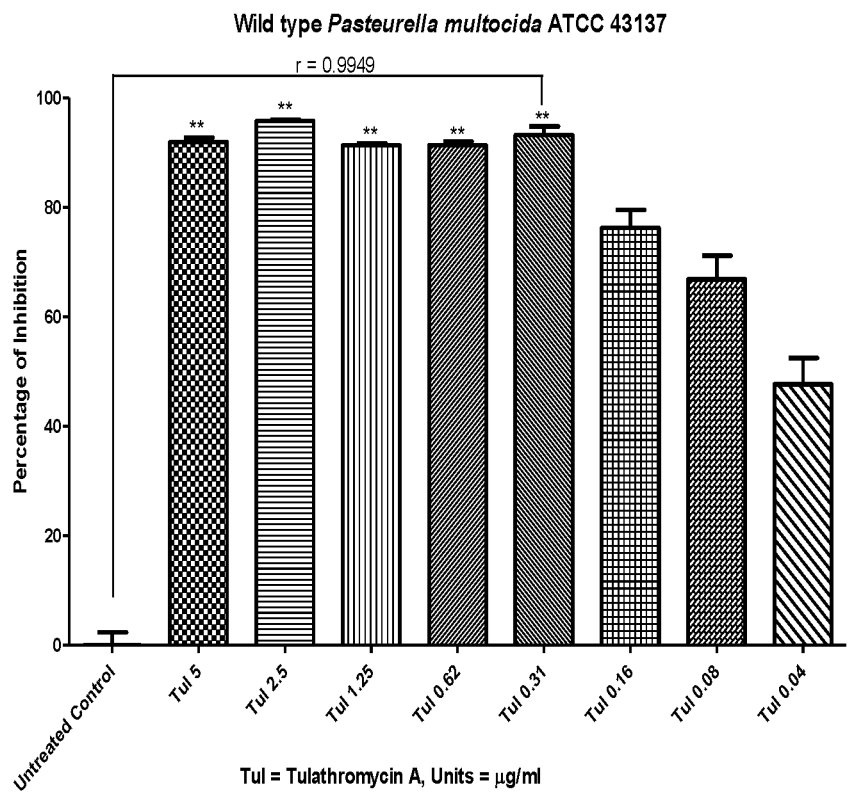
FIG. 1B is a bar graph for the determination of the minimum inhibitory concentration of tulathromycin (Tul) for *P. multocida*.
Figure 2A:
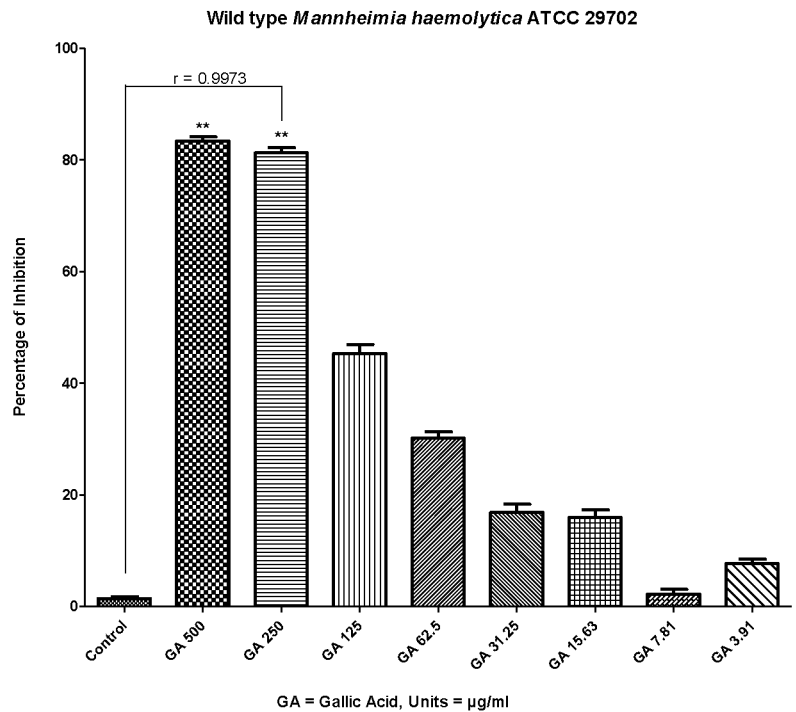
FIG. 2A is a bar graph for the determination of the minimum inhibitory concentration of gallic acid (GA) for *M. haemolytica*.
Figure 2B:
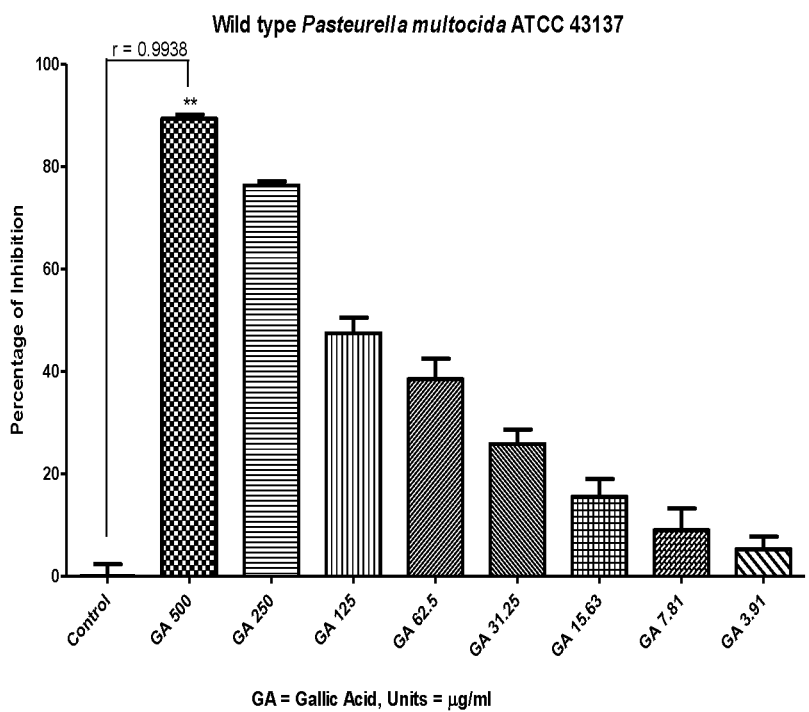
FIG. 2B is a bar graph for the determination of the minimum inhibitory concentration of gallic acid (GA) for *P. multocida*.

MIC of tulathromycin was found to be 0.31 µg/ml for both *M. haemolytica* and *P. multocida* (FIGS. 1A and 1B). MIC of Gallic acid was found to be 250 µg/ml for *M. haemolytica* (FIG. 2A) and 500 µg/ml for *P. multocida* (FIG. 2B).

(b) Antimicrobial Activity of Co-Culture *M. haemolytica* and *P. multocida*

Figure 3:
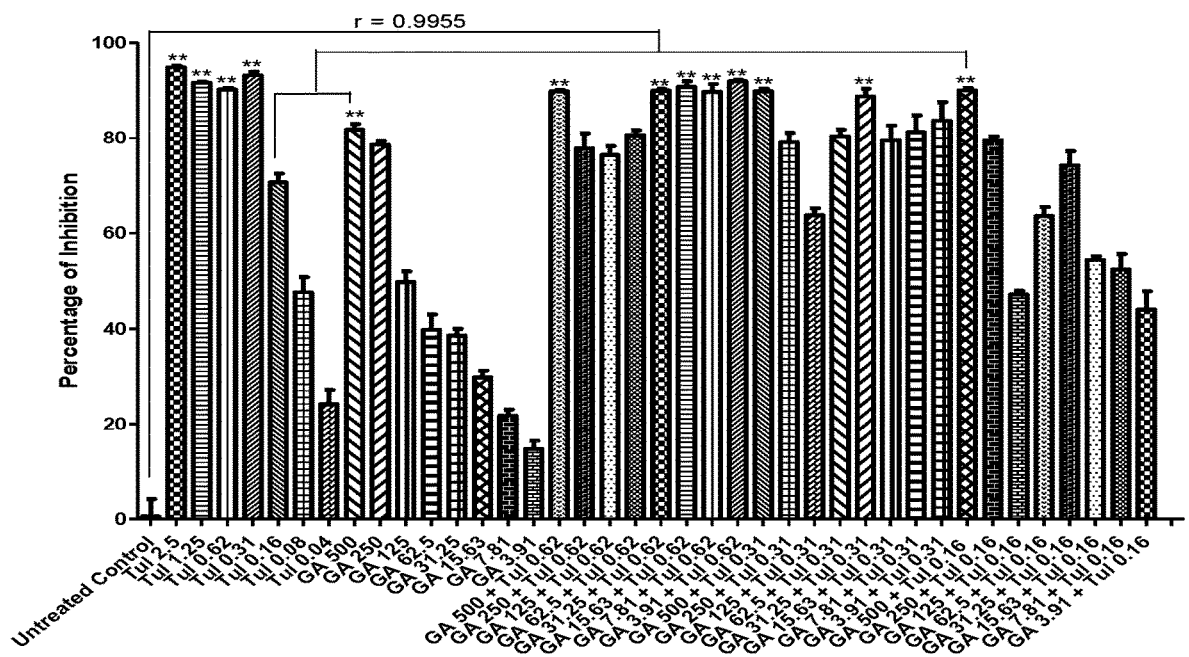
FIG. 3 is a bar graph for the determination of the minimum inhibitory concentration of Taluthromycin in combination with gallic acid is for of a co-culture of *M. haemolytica* and *P. multocida* in an exemplary embodiment of the application.

The MIC value of tulathromycin against co-culture of *M. haemolytica* and *P. multocida* was 0.31 µg/ml. Gallic acid has a MIC at 500 µg/ml against the co-culture. Interestingly, the combination of tulathromycin and gallic acid at a concentration of 0.16 µg/ml and 500 µg/ml, respectively had the best inhibition of the co-culture. This indicates that the combination of both the compounds can help reduce the concentration of the antibiotic half-fold. (FIG. 3)

(c) Synergistic Antibacterial Activity of Gallic Acid in Combination with Antibiotics The antibacterial activity of gallic acid against *M. haemolytica* and *P. multocida* was evaluated at several sub-MIC doses [250, 125, 62.5, 31.25, 15.6, 7.8 and 3.9 µg/ml] and in combination with sub-MIC doses of tulathromycin [5, 2.5, 1.25, 0.62, 0.31, 0.16, 0.08 and 0.04]. Broth micro dilution results using checker board assay show that gallic acid alone has less antibacterial activity against *M. haemolytica* and *P. multocida* where maximum reduction (7.70% and 5.33%) in bacterial growth was observed at 3.9 µg/ml dose. Antibacterial activity of gallic acid increased significantly in combination with tulathromycin and a reduction in bacterial growth (80.74% and 91.42%) was observed with addition of 0.16 µg/ml of tulathromycin in both the bacterial strains. (FIGS. 4A & 4B). The FIC index of the combination of tulathromycin and Gallic acid was found to be 0.516 and 0.508 for *M. haemolytica* and *P. multocida*, respectively. This suggests a borderline synergistic effect of these two drugs.

TABLE 1

Results of interaction studies between gallic acid + Tulathromycin against *M. haemolytica* and *P. multocida*.

| Gallic acid + Tulathromycin | | Gallic acid + Tulathromycin | |
|---|---|---|---|
| *M. haemolytica* | FIC Index | *P. multocida* | FIC Index |
| ATCC 29702 | 0.516 | ATCC 43137 | 0.508 |

$\text{FIC}_A$, $\text{FIC}_B$—Fractional inhibitory concentration of drug A & B respectively.
$\text{MIC}_A$, $\text{MIC}_B$—Minimum inhibitory concentration of drug A & B respectively.
[A], [B]—Concentration of drug A & B respectively.
The FIC indexes were interpreted as follows: synergy is defined as ≤0.5; additivity is defined as 0.5<4.0; and antagonism is defined as >4.

(d) Resistance Generation Study Results

Bacteria were treated individually with sub-MIC dose (½ MIC) of tulathromycin and gallic acid with alternate relaxation of stress in BHIB for 72 hrs each. Each 24 hrs treatment was considered as 1 generation (24 hrs drug+24 hrs of BHIB). It was observed that 3G *M. haemolytica* moderately looses its sensitivity to tulathromycin producing 17.16% resistance at 0.62 µg/ml (FIGS. 5A & 5B). In contrast, gallic acid treatment does not affect the sensitivity of bacteria. However, pre-treatment with tulathromycin and gallic acid did not alter the sensitivity of *P. multocida* (FIGS. 6A & 6B).

Discussion

The efficacy of tulathromycin as a metaphylactic antimicrobial in feedlot calves has been evaluated. Resistance due to tulathromycin, conferred by rRNA mutations in field isolates of *Mannheimia haemolytica* and *Pasteurella multocida* has been reported (J Antimicrob Chemother 2015; 70: 420-423). Tulathromycin resistant strains of *Mannheimia haemolytica* have been isolated from feedlot cattle (Front Microbiol. 2013 Oct. 9; 4:297. Vet Microbiol. 2017 September; 208:118-125). Towards this end, a novel antibiotic-phytochemical (tulathromycin-gallic acid) combination is proposed that can (1) help reduce the dosage of antibiotic to half fold (2) increase selection pressure (as it involves two drugs), and (3) is safe as it involves a phytochemical, that is a natural plant metabolite. Information on its possible mechanism of action is also provided.

Gallic acid is also an arginase inhibitor ($IC_{50}$ =2.2 µM). Local production of nitric oxide (NO) and other oxidants is enhanced in inflammatory diseases. (Conner E M and Grisham M B. Nutrition 1996; 12:274-277, Zhang Y, and Chen F. Cancer Res 2004; 64:1902-1905). It has been demonstrated recently that arginase is upregulated in allergic lung disease (Zimmermann N et al. J Clin Invest 2003; 111:1863-1874, King N E et al. J Nutr 2004; 134:2830S-2836S, and 2853S8). The functional significance of epithelial-dependent NF-κB activation in lung inflammation and allergic lung disease has also been documented. Chronic inflammatory diseases that are accompanied by NF-κB activation and upregulation of arginases may be affected by regulation of NF-κB through arginase-dependent regulation of NO levels (Ckless et al. Am. J. Respir. Cell Mol Biol 36 (6) p 645-653 2007)

Gallic acid seems to have multiple targets and may act, for example, by reducing inflammation in the host lung cells as well as inhibiting key enzymes in the BRD pathogens. The data herein indicates that combining tulathromycin with gallic acid shows symbiotic activity. Since new antibiotics are lacking in the market, and the pharmaceutical industry is reluctant to introduce new antimicrobial drugs, there is a need to develop new strategies for treating resistant bacteria. Possibly, existing antibiotics for which bacteria have developed resistance could be repositioned or used in combination with safer treatment options. Also, previously it was suggested that decreased usage of antibiotics can limit resistance development and prevent or delay the emergence of resistance (J Antimicrob Chemother, 59, 825-826). The present investigation is a step forward in this direction.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

CITATIONS FOR DOCUMENTS REFERRED TO IN THE DESCRIPTION

1. Li, A. N., Li, S., Zhang, Y. J., Xu, X. R., Chen, Y. M., & Li, H. B. 2014. Resources and biological activities of natural polyphenols. Nutrients. 22, 6020-6047.
2. Langeveld, W. T., Veldhuizen, E. J., & Burt, S. A. 2014. Synergy between essential oil components and antibiotics: a review. Crit. Rev. Microbiol. 40, 76-94.
3. Venkatadri, B., Arunagirinathan, N., Rameshkumar, M. R., Ramesh, L., Dhanasezhian, A., & Agastian, P. 2015. In vitro Antibacterial Activity of Aqueous and Ethanol Extracts of *Aristolochia indica* and *Toddalia asiatica* Against Multidrug-Resistant Bacteria. Indian J. Pharm. Sci., 77, 788-791.
4. Dey, D., Ghosh, S., Ray, R., & Hazra, B. 2016. Polyphenolic Secondary Metabolites Synergize the Activity of Commercial Antibiotics against Clinical Isolates of β-Lactamase-producing *Klebsiella pneumoniae*. *Phytother. Res.*, 30, 272-282.
5. Barreto, H. M., Coelho, K. M., Ferreira, J. H., Dos Santos, B. H., de Abreu, A. P., Coutinho, H. D., da Silva, R. A., de Sousa, T. O., Citó, A. M., & Lopes, J. A. 2016. Enhancement of the antibiotic activity of aminoglycosides by extracts from *Anadenanthera colubrine* (Vell.) Brenan var. cebil against multi-drug resistant bacteria. Nat. Prod. Res., 30, 1289-1292. 28.
6. Ganesan, A. 2008. The impact of natural products upon modern drug discovery. Curr. Opin. Chem. Biol., 12, 306-317.
7. Brötz-Oesterhelt, H. & Brunner, N. A. 2008. How many modes of action should an antibiotic have? Curr. Opin. Pharmacol., 8, 564-573.
8. Hopkins, A. L. 2008. Network pharmacology: The next paradigm in drug discovery. Nat. Chem. Biol., 4, 682-690. 31.
9. Pokrovskaya, V. & Baasov, T. 2010. Dual-acting hybrid antibiotics: A promising strategy to combat bacterial resistance. Expert Opin. Drug Discov., 5, 883-902.
10. Borges A, Ferreira C, Saavedra M J, Simões M. Antibacterial activity and mode of action of ferulic and gallic acids against pathogenic bacteria. Microb Drug Resist. 2013; 19:256-65.
11. Jayaraman, P. et al. Int. J. Biol. Sci. 2010, 6:556-568

The invention claimed is:

1. A method of treating or preventing a *Mannheimia haemolytica* and/or *Pasteurella multocida* bacterial infection or a disease, disorder or condition arising from a *Mannheimia haemolytica* and/or *Pasteurella multocida* bacterial infection comprising administering an effective amount of tulathromycin, or a pharmaceutically acceptable salt, prodrug and/or solvate thereof, in combination with an effective amount of gallic acid or a pharmaceutically acceptable salt and/or solvate thereof, to a subject in need thereof.

2. The method of claim 1, wherein the gallic acid is in the form of the free acid or a pharmaceutically acceptable base addition salt of the free acid.

3. The method of claim 1, wherein the bacterial infection is an infection of at least one bacterium belonging to the species *Mannheimia hemolytica* and at least one bacterium belonging to the species *Pasteurella multocida*.

4. The method of claim 1, wherein the subject is an animal.

5. The method of claim 1, wherein the disease, disorder or condition is selected from one or more of bovine respiratory disease, bovine mastitis, shipping fever, and other bovine pasteurellosis conditions.

6. The method of claim 1, wherein the disease is bovine respiratory disease.

7. A method of improving the efficacy of tulathromycin for treating or preventing a *Mannheimia haemolytica* and/or *Pasteurella multocida* bacterial infection or a disease, disorder or condition arising from a *Mannheimia haemolytica* and/or *Pasteurella multocida* bacterial infection comprising administering an effective amount of tulathromycin, or a pharmaceutically acceptable salt, prodrug and/or solvate thereof, in combination with an effective amount of gallic acid or a pharmaceutically acceptable salt and/or solvate thereof, to a subject in need thereof.

8. A pharmaceutical composition comprising tulathromycin or a pharmaceutically acceptable salt, prodrug and/or solvate thereof, and gallic acid or a pharmaceutically acceptable salt and/or solvate thereof wherein the tulathromycin and gallic acid are present in amounts that are synergistically effective to treat a *Mannheimia haemolytica* and/or *Pasteurella multocida* bacterial infection, or a disease, disorder or condition arising from a *Mannheimia haemolytica* or *Pasteurella multocida* bacterial infection.

9. A kit for the treatment of a *Mannheimia haemolytica* and/or *Pasteurella multocida* bacterial infection or a disease, disorder or condition arising from a *Mannheimia haemolytica* and/or *Pasteurella multocida* bacterial infection, in a subject in need thereof, the kit comprising: gallic acid or a pharmaceutically acceptable salt and/or solvate thereof; tulathromycin or a pharmaceutically acceptable salt, prodrug and/or solvate thereof; and instructions for contemporaneous administration of the gallic acid or pharmaceutically acceptable salts and/or solvates thereof and the tulathromycin, or pharmaceutically acceptable salts, prodrugs and/or solvates thereof, to the subject in need thereof.

10. A kit for improving the efficacy of tulathromycin for the treatment of a *Mannheimia haemolytica* and/or *Pasteurella multocida* bacterial infection or a disease, disorder or condition arising from a *Mannheimia haemolytica* and/or *Pasteurella multocida* bacterial infection, in a subject in need thereof, the kit comprising: tulathromycin or a pharmaceutically acceptable salt, prodrug and/or solvate thereof; gallic acid or a pharmaceutically acceptable salt and/or solvate thereof; and instructions for contemporaneous administration of the tulathromycin or pharmaceutically acceptable salts, prodrugs and/or solvates thereof and the gallic acid or pharmaceutically acceptable salts and/or solvates thereof, to the subject in need thereof.

11. The kit of claim 9, wherein the tulathromycin or pharmaceutically acceptable salt, prodrug and/or solvate thereof; and gallic acid, or pharmaceutically acceptable salt and/or solvate thereof; are formulated in a single dosage form.

12. The kit of claim 9, wherein the tulathromycin or pharmaceutically acceptable salt, prodrug and/or solvate thereof; and gallic acid, or pharmaceutically acceptable salt and/or solvate thereof; are formulated in separate dosage forms.

13. The kit of claim 10 wherein the tulathromycin or pharmaceutically acceptable salt, prodrug and/or solvate thereof; and gallic acid, or pharmaceutically acceptable salt and/or solvate thereof; are formulated in a single dosage form.

14. The kit of claim 10, wherein the tulathromycin or pharmaceutically acceptable salt, prodrug and/or solvate thereof; and gallic acid, or pharmaceutically acceptable salt and/or solvate thereof; are formulated in separate dosage forms.

15. The method of claim 1, wherein the tulathromycin or pharmaceutically acceptable salt, prodrug and/or solvate thereof; and gallic acid, or pharmaceutically acceptable salt and/or solvate thereof; are formulated in a single dosage form.

16. The method of claim 1, wherein the tulathromycin or pharmaceutically acceptable salt, prodrug and/or solvate thereof; and gallic acid, or pharmaceutically acceptable salt and/or solvate thereof, are formulated in separate dosage forms.

17. The method of claim 7, wherein the tulathromycin or pharmaceutically acceptable salt, prodrug and/or solvate thereof; and gallic acid, or pharmaceutically acceptable salt and/or solvate thereof; are formulated in a single dosage form.

18. The method of claim 7, wherein the tulathromycin or pharmaceutically acceptable salt, prodrug and/or solvate thereof; and gallic acid, or pharmaceutically acceptable salt and/or solvate thereof, are formulated in separate dosage forms.

19. The method of claim 7, wherein the disease, disorder or condition is selected from one or more of bovine respiratory disease, bovine mastitis, shipping fever, and other bovine pasteurellosis conditions.

20. The method of claim 7, wherein disease is bovine respiratory disease.

* * * * *